United States Patent [19]

Müller

[11] Patent Number: 4,715,216
[45] Date of Patent: Dec. 29, 1987

[54] PROCESS AND APPARATUS FOR THE CHROMATOGRAPHIC DETERMINATION OF COMPONENTS IN SPECIMENS

[75] Inventor: Klaus P. Müller, Jülich, Fed. Rep. of Germany

[73] Assignee: Kernforschungsanlage Jülich Gesellschaft mit beschränkter Haftung, Jülich, Fed. Rep. of Germany

[21] Appl. No.: 799,491

[22] Filed: Nov. 19, 1985

[30] Foreign Application Priority Data

Nov. 19, 1984 [DE] Fed. Rep. of Germany ....... 3442227

[51] Int. Cl.⁴ ............................................ G01N 31/08
[52] U.S. Cl. .................................. 73/61.1 C; 422/70; 436/161
[58] Field of Search ...................... 73/61.1 C; 422/70; 436/161; 210/198.3

[56] References Cited

U.S. PATENT DOCUMENTS

| | | | |
|---|---|---|---|
| 3,419,051 | 12/1968 | Gustafson et al. | 73/61.1 C |
| 3,923,460 | 12/1975 | Parrott et al. | 73/61.1 C |
| 4,032,445 | 6/1977 | Munk | 73/61.1 C |
| 4,043,906 | 8/1977 | Helmer | 73/61.1 C |
| 4,165,219 | 8/1979 | Huber | 73/61.1 C |
| 4,239,623 | 12/1980 | Schrenker | 73/61.1 C |
| 4,267,056 | 5/1981 | McClure | 422/70 |
| 4,427,298 | 1/1984 | Fahy et al. | 366/142 |

FOREIGN PATENT DOCUMENTS

| | | | |
|---|---|---|---|
| 44347 | 3/1983 | Japan | 422/70 |
| 87458 | 5/1983 | Japan | 422/70 |
| 178255 | 10/1983 | Japan | 422/70 |

OTHER PUBLICATIONS

Erich Heftmann; A Laboratory Handbook of Chromatographic & Electrophoretic Methods, Third Edition.

Primary Examiner—Stewart J. Levy
Assistant Examiner—Hezron E. Williams
Attorney, Agent, or Firm—Nils H. Ljungman

[57] ABSTRACT

For the determination of low ion concentrations in aqueous specimens by ion chromatography with aqueous eluents, the test specimen is added to a stream of extra-pure water, which is mixed immediately ahead of the separation column with an appropriately concentrated eluent. Alternatively, the ions are previously fixed to an adsorber, and eluted from the more highly concentrated eluent, which is again mixed ahead of the separation column with extra-pure water to achieve the concentration necessary for ion chromatography. For such a pre-enrichment, there are two small pre-enrichment columns, which are flowed through by extra-pure water containing the specimen or concentrated eluents alternately in reverse directions from analysis cycle to analysis cycle. An additional purification of the extra-pure water and eluent feed is recommended, as is a pulsation damping by a membrane of a two-headed pump located between the eluent branch and the extra-pure water branch, each with a volume of approximately 1.5 to 2 times the pump stroke.

19 Claims, 10 Drawing Figures 0    10 min

PROCESS AND APPARATUS FOR THE CHROMATOGRAPHIC DETERMINATION OF COMPONENTS IN SPECIMENS

BACKGROUND OF THE INVENTION

1. Field of the Invention

The invention relates to a process for the determination of small ion concentrations in aqueous specimens by ion chromatography with an aqueous eluent, and also to an apparatus for the execution of the process.

2. Description of the Prior Art

Aqueous specimens, specifically those which are obtained from the environment, such as atmospheric condensates, bored ice cores from glaciers, or hailstones, contain trace amounts of ionic impurities, the measurement of which is extraordinarily important for a determination of current conditions and changes relative to previous measurements.

In terms of order of magnitude, such trace impurities may lie in the range of ppb (parts per billion, or $1 \times 10^{-9}$) so that the sensitivity of the analysis equipment must be high. Commercial devices generally have their detection limits in the range of 100 ppb.

FIG. 6 shows the curve of the conductivity of fluid exiting the separation column of the chromatograph in a conventional method of operation. It can be seen that, at the beginning of the chromatogram, there is a severe drop in conductivity. This is caused by the low conductivity of the water of the specimen, which is normally added into the eluent current.

According to the invention, this decrease in conductivity is prevented as a result of the fact that a stream of concentrated eluent is conducted to the column, which is diluted to the desired concentration prior to introduction into the column with a stream of extra-pure water into which the specimen is introduced prior to mixing. In this manner, the water of the specimen itself presents no further interference during the following chromatographic process. Extra-pure water is water which has been freed of impurities as far as possible, and whose level of impurities will not interfere with the intended detection, that is, water whose concentration of impurities can no longer be detected by the measurement apparatus. This type of water for analysis is produced in a known manner by multiple distillation and/or ion exchange processes, and may be obtained from the Fa. Millipore as "Milli-Q", especially type 1, having an electrical resistivity of 16.66 meg-ohm per cm. The chromatogram illustrated in FIG. 6 for anions can, of course, also be taken with an appropriate column packing and elution agent for cations.

OBJECTS OF THE INVENTION

It is therefore an object of the invention to improve the sensitivity of present chromatographic devices.

Is is another object of the invention to provide a unique method for chromatographic analysis and an improved apparatus for effecting the same.

It is yet another object of the invention to provide an improved technique for pulsation damping with two-headed delivery pumps.

SUMMARY OF THE INVENTION

The process developed by the invention for this purpose is characterized by the fact that a more highly-concentrated eluent is mixed with a corresponding amount of extra-pure water ahead of the separation column of the ion chromatograph, whereby the aqueous specimen solution is added to the extra-pure water stream, or the ions contained in the specimen solution are preliminarily fixed on an adsorber eluted from the more highly concentrated eluent. The invention also provides an apparatus whereby the aforementioned process is effected. In this manner, the decrease in conductivity which is caused by the water content of the specimen and which adversely affects the measurement of the rapidly migrating ions is eliminated and, with additional preliminary fixing, an increase in sensitivity is achieved with peaks which become more narrow.

Preferably, for such a preliminary fixing of the ions contained in the specimen water, two small pre-enrichment columns are used. These columns are located between the specimen feed and the separation column, and can be included alternately with a change of direction in the stream of extra-pure water and the stream of more concentrated eluent respectively. The ions originating from the specimen are thereby fixed out of the extra-pure water current on the pre-enrichment column, and in the next cycle, are carried along by highly-concentrated eluent.

The inclusion of an additional purification column upstream is particularly effective, specifically in the stream of extrapure water. Preferably, however, there is a purification column in the feed stream of the concentrated eluent, and also in the stream of extra-pure water, which are alternately reversed. Impurities are captured by the purification columns from the extra-pure water stream, which are carried along in a thrust during the reversal by the more highly-concentrated eluents, so that after this intermediate phase, particularly clean conditions can be maintained for subsequent analyses.

BRIEF DESCRIPTION OF THE DRAWINGS

The above as well as other features and advantages of the present invention can be fully appreciated through consideration of the detailed description of the invention in conjunction with the accompanying drawings, in which.

DESCRIPTION OF THE PREFERRED EMBODIMENTS

Figure 1:
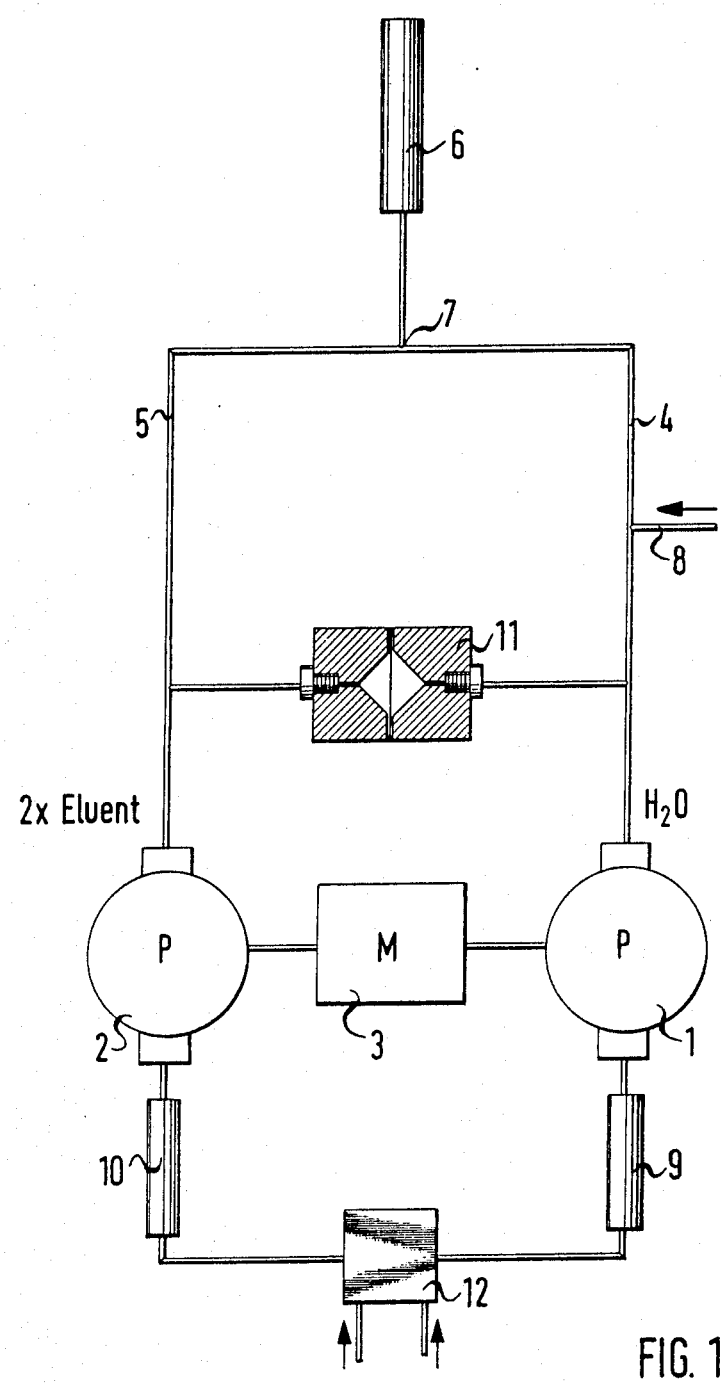
FIG. 1 is a schematic illustration of an apparatus for the execution of the process of this invention with purification columns and pulsation damping, but without pre-enrichment columns.

A diagram of an apparatus for the execution of the process described by the invention is shown in FIG. 1. By means of pump heads 1 and 2, driven by a motor 3, extra-pure water is transported through a line 4, and double-concentrated eluent through a line 5 to a separation column 6. The extra-pure water and double-concentrated eluent are mixed with one another at 7. The aqueous analysis specimen is added to the extra-pure water line at 8. By extra-pure water is meant water in which the concentration of impurities can no longer be detected by the measurement apparatus. Such water is produced by conventional techniques through multiple distillation and/or ion exchange processes. Pump heads which can be used for ion chromatography are commercially available, and are manufactured by, among others, the Dionex Company. Dionex GmbH has a branch located at Einsteinstrasse, 6108 Weiterstadt, Federal Republic of Germany. American Dionex Corporation is located at 1238 Titan Way, P.O. Box 3603, Sunnyvale, Calif. 91088-3603.

In this symmetrical configuration, in which the same amount of eluent and extra-pure water are transported, the eluent is concentrated double. Of course, other mixing ratios and concentrations can also be selected.

Preferably, purification columns 9 and 10 are included in the lines leading to the pump for extra-pure water and concentrated eluent. A membrane arrangement 11, located between the lines 4 and 5, is used for pulsation damping, and is illustrated in greater detail in FIGS. 4a and 4b.

With this completely symmetrical arrangement, both branches (extra-pure water and eluent branch) can be switched with one another, for which purpose there is a reversal apparatus 12.

As a result of the mixing of concentrated eluent with water described above, a broadening of the "peaks" is observed in the chromatogram, as will be described in connection with FIGS. 5a–5d below.

Figure 2:
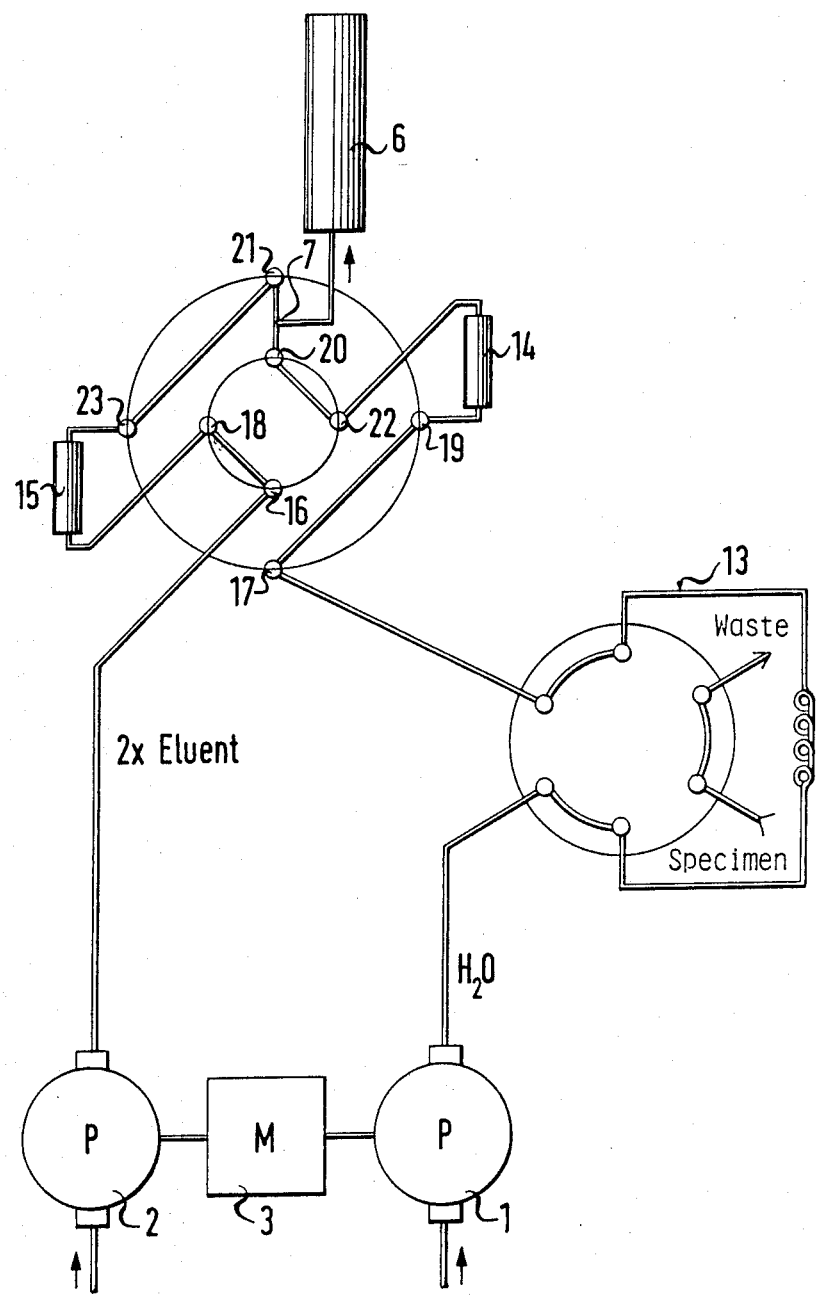
FIG. 2 is a schematic illustration of an alternative configuration of the apparatus of this invention with pre-enrichment columns.

According to a refinement of the invention, this can be prevented and an additional increase in sensitivity can be achieved by providing for a preliminary fixing of the ions, specifically with the apparatus illustrated in FIG. 2, in which a pair of enrichment columns and a four-way valve "V" are located ahead of the separating column 6. Such a valve is e.g. manufactured by the Packard Co. under the designation GC sampling valve.

During the operation of this apparatus shown in FIG. 2, in the position shown, a specimen fed through a specimen feed apparatus 13 (approximately 10–1000 microliters) is carried along by the extra-pure water stream to the column 14 where the specimen ions are fixed, whereas the extra-pure water (freed from the ions to be detected) goes to the mixing point 7, where it is mixed with the eluent, which flows through the column 15. Thereby it picks up the specimen from the previous cycle enriched in the column 15. Specimen feed valves are known in the art, and are available commercially e.g. from Valco Instruments Company, Inc. or from the Dionex Company.

The columns 14 and 15 are identical, so that the one always acts as a pressure equalizer for the other in the circuit illustrated. In this manner, no different pressure decreases will be produced in both lines (for extra-pure water and for eluents).

The pre-enrichment columns 14 and 15 are as small as possible, less than 10 cubic centimeters, and have a separation bed length of, for example, 3 cm with a free width of 4 mm.

The double-column configuration is particularly preferred, but not mandatory. In a different arrangement of the circuit, there can be only a single pre-enrichment column.

Considering FIG. 2, the operation of the four-way valve "V" and the pre-enrichment columns 14 and 15 will now be described.

The specimen is conveyed from the specimen feed apparatus 13 through line 8 to valve point 17, from which it is directed to point 19, and then to the pre-enrichment column 14, where it (the ions contained) is fixed, the ion feed extra-pure water is conveyed from the pre-enrichment column 14 to point 22 to point 20, and then to mixing point 7, where it is mixed with the eluent. The eluent is conveyed from the pump head 2 through line 5 to point 16 of valve "V". The eluent then flows from point 16 to point 18 through the column 15 eluting the fixed specimen ions of the preceding cycle, then through points 23 and 21 to the mixing point 7. From the mixing point 7, the mixture of the eluent with the specimen and the extra-pure water are conveyed to the separating column 6.

With the configuration illustrated in FIG. 2, after the completion of the analysis of the specimen material carried along by the double-concentrated eluent in one thrust from the enrichment column 15, the flow is reversed, so that in the next cycle, the column 15 is placed in the extra-pure water circuit with the specimen feed apparatus 13, while the pre-enrichment column 14 is then switched into the eluent branch. After the reversal, the points 17–23, 19–21, 16–22 and 18–20 are connected to one another, and the columns 14 and 15 each carry the stream in the reverse direction. More particularly, after the reversal, the specimen feed apparatus 13 introduces the specimen into line 8 and the valve "V" at point 17 thereof. The four-way valve has now been adjusted so that the fluid path is reversed from that previously described. That is to say, the fluid now flows from point 17 to point 23 and into column 15, in which the direction of flow is reversed from that previously described in connection with the eluent. From the bottom of column 15, the specimen freed water flows to point 18, then to point 20, and finally to the mixing point 7. The eluent from the pump head 2 travels through line 5, where it enters the valve "V" at point 16, and then onto point 22, whereupon the eluent is directed through the column 14, from the top to the bottom eluting the specimen ions of the preceding cycle fixed at the bottom end of the column 14, and re-enters the valve "V" at point 19. The eluent then flows from point 19 to point 21 of the valve, where it is on the opposite side of the mixing point 7 with respect to the previously described circuit flow. Both the specimen ion containing eluent and the extra-pure water are mixed at point 7, and then directed to the separating column 6.

As shown in the configuration in FIG. 1, in the feed line of the concentrated eluent and of the extra-pure water, preferably there are purification columns 9 and 10 which are ahead of the pump, each of which is packed with a strong ion exchanger. Lewatit$^{(R)}$ from the Merck Company, Darmstadt, Federal Republic of Germany, provides acceptable units for the process and apparatus described herein. Pulsation damping (similar to 11 in FIG. 1) is also appropriate here.

The eluent can be, for example, a carbonate/hydrogen carbonate solution for the elution of anions from an anion exchanger column with a weak, cross-linked ion exchanger.

Similarly, a determination of cations could also be made with a cation exchanger, whereby dilute nitric acid could then be used as the eluent.

The separation columns 6 were operated at pressures between 40 and 60 bar. Columns manufactured by the Dionex Company were used. The practically symmetrical line layouts in the four-way valve "V" and the identical pre-enrichment columns 14, 15 result in identical pressure conditions in both lines. With the symmetrical configuration, the residual fluids from phase or the other remaining in the connecting lines are also equalized. Otherwise, these connecting lines are kept as short as possible.

With the configuration according to the invention, the ions eluted earliest, such as fluoride, chloride and nitrite, can be determined down to about 0.1 ppb, even with the simple configuraton illustrated in FIG. 1. With the configuration illustrated in FIG. 2, an increase in sensitivity for all ions is achieved up to 0.01 ppb, with an analysis time of 10 minutes.

FIGS. 5a, 5b, 5c and 5d show four anion chromatograms of specimens with different specimen concentrations which are, for 5a and 5b, 100 ppb or 10 ppb anions, respectively, in a specimen volume of 10 microliters, and for 5c and 5d, 1 ppb or 0.1 ppb, respectively, in a 500 microliter specimen volume. The detector sensitivity was 3 microsiemens for 5a and 5c, and 1 microsiemens for 5b and 5d.

Figure 4A:
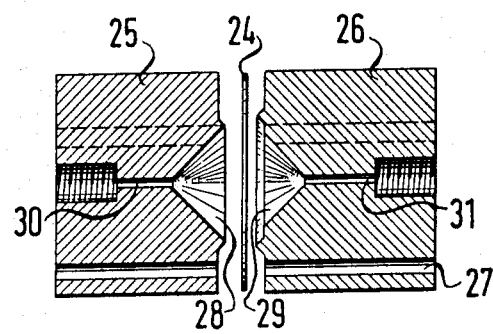
FIGS. 4a and 4b are detailed schematic representations of a damping membrane apparatus.
Figure 4B:
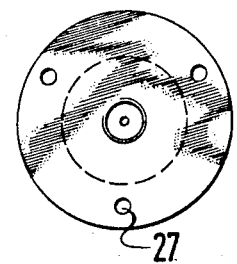
Figure 5A:
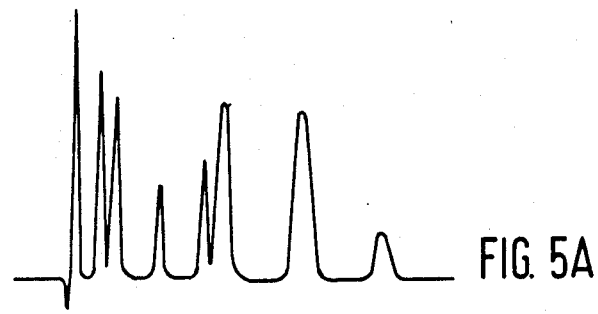
FIGS. 5a, 5b, 5c and 5d are chromatograms of specimens with different concentrations of impurities obtained using the process of this invention.
Figure 5B:
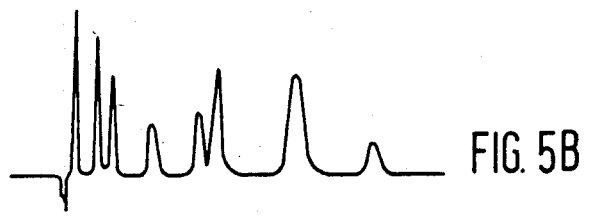
Figure 5C:
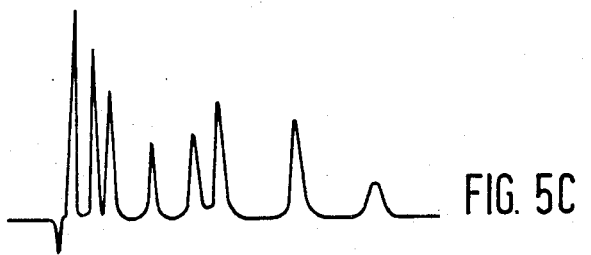
Figure 5D:
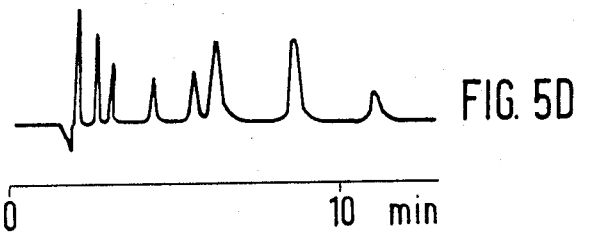
Figure 6:
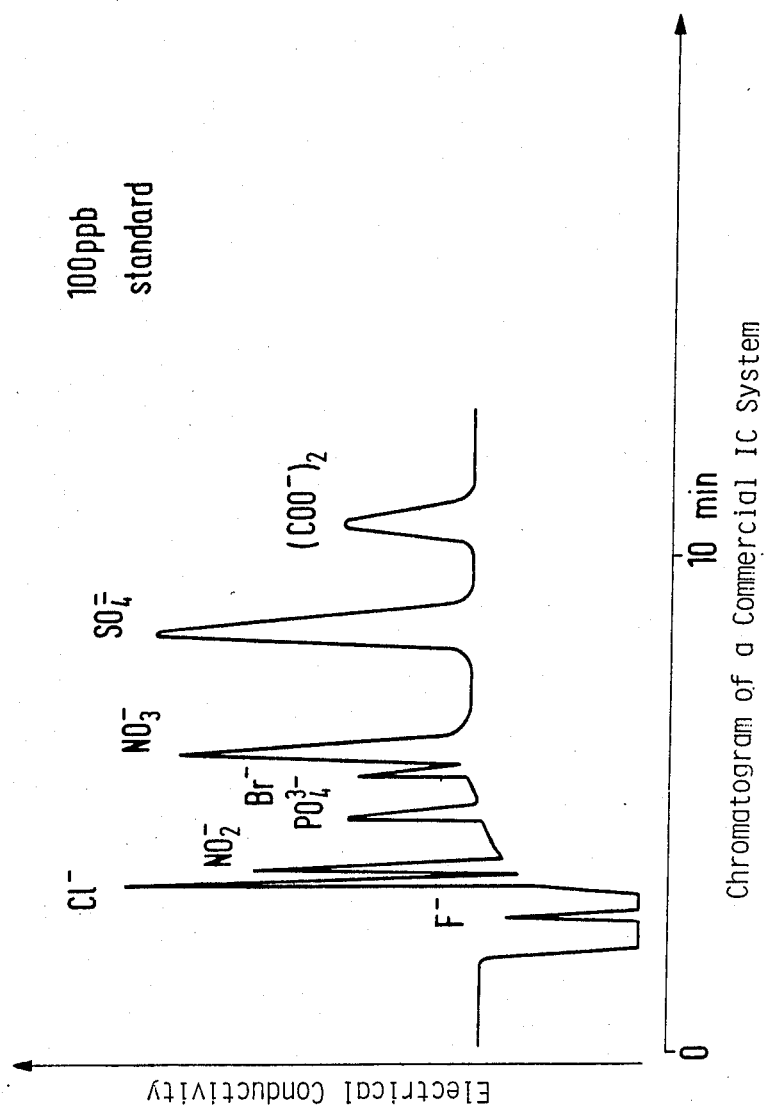
FIG. 6 is a chromatogram which was taken with a conventional, prior art system.

The membrane indicated for the pulsation damping in FIG. 1 is illustrated in greater detail in FIGS. 4a and 4b. A teflon membrane 2 which is 0.3 mm thick, for example, is braced between two connecting pieces 25 and 26, which are held by screws inserted in holes 27. The connection pieces 25 and 26 form equalization volumes 28 and 29 on each side of the membrane 2, of about 1.5 to 2 times the pump stroke, for example, 100 microliters, which are in communication with the lines 4 or 5 (as shown in FIG. 1) via capillaries 30 and 31. The membrane 2 need not withstand any large pressures, since it needs to equalize only small pressure differences (approximately 1 to 2 bar) between the two stroke chambers of the double-piston pump. Its size and thickness are a function of the equalization work to be performed.

Figure 3:
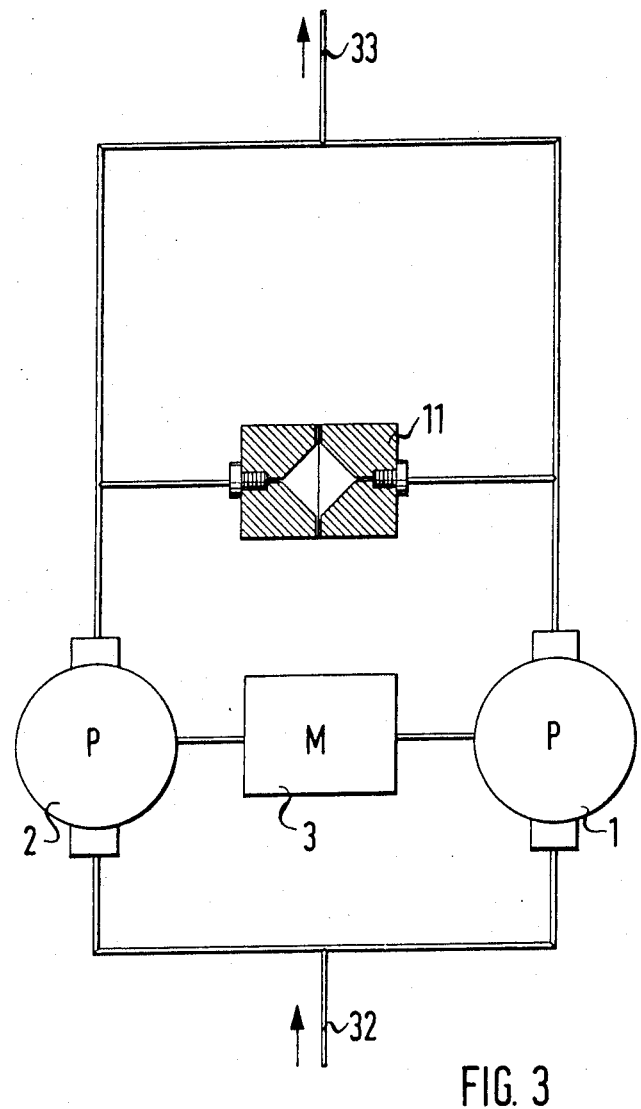
FIG. 3 is a schematic diagram of a pump with pulsation damping by means of a membrane.

Such a pulsation damping by means of a membrane is favourable for double-piston pumps, specifically with a low delivery, and can be used for applications other than ion chromatography. FIG. 3 shows a diagram for such a delivery pump with input 32 and output 33 having a stroke volume damped by a damping membrane. Such pulsation damping is preferable to the customarily-used stainless steel damping spirals or gas-pressurized membrane dampers, which exhibit a large elastic volume and which can cause short-term pressure fluctuations during reversing processes, sice, in the latter case, unreproducible quantities of fluid are emitted into the flow system.

According to the invention, the damping membrane with a small equalization volume, especially with the transport system of different components to be measured, leads to a stable concentration of the mixture produced from the transported ingredients.

The invention as described hereinabove in the context of the preferred embodiments is not to be taken as limited to all of the provided details thereof, since modifications and variations thereof may be made without departing from the spirit and scope of the invention.

The invention described above for the separation of very small ionic components of an aqueous specimen by ion chromatography could of course used more generally for any separation of components (small or large, ionic or not) by chromatographic methods including HPLC or else contained in any solvent perhaps organic solvent as ethanol or alcanes or other.

The aqueous specimens to be analyzed must not be originally liquid or aqueous but could likewise be at first in solid form.

What is claimed is:

1. In a process for the determination of component concentrations down to the ppb (1 part per $10^9$ parts) range of a liquid specimen by chromatography separating said components in a separation column by means of an eluent stream of adapted special concentration, said specimen being at once introduced into the liquid stream to the separation column, the improvement comprising the steps of:
   providing a stream of said eluent with a concentration higher than said adapted special concentration for chromatographic separation; and
   mixing said higher concentrated eluent stream with a necessary stream of extra-pure solvent to achieve said adapted special concentration when introducing the mixed streams into said separation column;
   said liquid specimen being added to said extra-pure solvent stream, just before mixing.

2. In a process for the determination of ion concentrations down to the ppb (1 part per $10^9$ parts) range of an aqueous specimen by ion chromatography separating the components in a separation column by means of an aqueous eluent stream of adapted special concentration, said aqueous specimen being at once introduced into the liquid stream to the separation column, the improvement comprising the steps of:
   providing a stream of said aqueous eluent with a concentration higher than said adapted special concentration for chromatographic separation; and
   mixing said higher concentrated eluent stream with a necessary stream of extra-pure water to achieve said adapted special concentration when introducing the mixed streams into said separation column;
   said aqueous specimen solution being added to said extra-pure water stream, just before mixing.

3. In a process for the determination of component concentrations down to the ppb (1 part per $10^9$ parts) range of a liquid specimen by chromatography separating said components in a separation column by means of an eluent stream of adapted special concentration, said specimen being at once introduced into the liquid stream to the separation column, the improvement comprising the steps of:
   providing a stream of said eluent with a concentration higher than said adapted special concentration for chromatographic separation; and
   mixing said higher concentrated eluent stream with a necessary stream of extra-pure solvent to achieve said adapted special concentration when introducing the mixed streams into said separation column;
   the components to be detected of said specimen solution being preliminarily fixed on an adsorber eluted by said higher concentrated eluent stream prior to mixing with said extra-pure solvent stream.

4. In a process for the determination of small ion concentrations down to the ppb (1 part per $10^9$ parts) range of an aqueous specimen by ion chromatography separating components in a separation column by means of an aqeuous eluent stream of adapted special concentration, said aqueous specimen being at once introduced into the liquid stream to the separation column, the improvement comprising the steps of:
   providing a stream of said aqueous eluent with a concentration higher than said adapted special concentration for chromatographic separation; and mixing said higher concentrated eluent stream with a necessary stream of extra-pure water to achieve said adapted special concentration prior to introduction into said separation column;

the ions to be detected of said aqueous specimen solution being preliminarily fixed on an adsorber eluted by said higher concentrated eluent stream prior to mixing with said extra-pure water stream.

5. The improved process according to claim 4 wherein the step of preliminarily fixing the ions is effected by means of first and second pre-enrichment columns.

6. The improved process according to claim 5 wherein said first and second pre-enrichment columns are so interconnected that the flow of more concentrated eluent and extra-pure water therethrough is reversed from analysis cycle to analysis cycle, whereby the ions from the extra-pure water stream fixed in one of said pre-enrichment columns are carried along in the next cycle by said more concentrated eluent to said separation column.

7. The improved process according to claim 2 wherein both the extra-pure water stream and the correspondingly more concentrated eluent stream are each preliminarily conveyed through a purification column upstream.

8. The improved process according to claim 4 wherein both the extra-pure water stream and the correspondingly more concentrated eluent stream are each preliminarily conveyed through a purification column upstream.

9. An apparatus for use in combination with a separation column of a chromatograph for the detection of components down to the ppb-range (1 part per $10^9$ parts) in a specimen solution, said apparatus comprising:

a two-headed feed pump means, operating at a constant flow rate;

first conduit means for the transport of a more concentrated eluent from said two-headed feed pump means to a mixing point;

second conduit means for the transport of extra-pure solvent from said two-headed feed pump means to said mixing point; and specimen feed apparatus means disposed between said two-headed feed pump means and the mixing means, whereby the specimen of interest is introduced into said extra-pure solvent prior to the mixing point, wherein the extra-pure solvent is combined with said more concentrated eluent for introduction into said separation column.

10. The apparatus according to claim 9 including a first and second pre-enrichment column disposed upstream of said separation column.

11. The apparatus according to claim 10 including valve means disposed between said first and second pre-enrichment columns and said two-headed feed pump means, said valve means altering connection of said pre-enrichment columns into the stream of more concentrated eluent or extra-pure solvent with a change in the direction of flow through said pre-enrichtment columns.

12. The apparatus according to claim 9 including a purification column with a strong decontaminating means disposed in each of the feed lines for the more concentrated eluent and extra-pure solvent.

13. The apparatus according to claim 9 including a damping means disposed between said first conduit and second conduit means.

14. The apparatus according to claim 13 wherein the damping means is a damping membrane means which defines an equalization volume which is at least equal to the stroke volume of said feed pump means.

15. The apparatus according to claim 9 including a purification column with a strong ion exchanger disposed in each of the feed lines for the more concentrated eluent and extra-pure water.

16. The apparatus according to claim 15 wherein said equalization volume is 1.5 to 2 times the stroke volume.

17. In a process for the determination of small ion concentrations down to the ppb (1 part per $10^9$ parts) range of an aqueous specimen by ion chromatography separating components in a separation column by means of an aqueous eluent stream of adapted special concentration, said aqueous specimen being at once introduced into the liquid stream to the separation column, the improvement comprising the steps of:

providing a stream of said aqueous eluent with a concentration higher than said adapted special concentration for chromatographic separation; and mixing said higher concentrated eluent stream with a necessary stream of extra-pure water to achieve said adapted special concentration prior to introduction into said separation column;

the ions to be detected of said aqueous specimen solution being preliminarily fixed on an adsorber eluted by said higher concentrated eluent stream prior to mixing with said extra-pure water stream, wherein the step of preliminarily fixing the ions is affected by means of first and second pre-enrichment columns which are so interconnected that the flow of more concentrated eluent and extra-pure water therethrough is reversed from analysis cycle to analysis cycle, whereby the ions from the extra-pure water stream fixed in one of said pre-enrichment columns are carried along in the next cycle by said more concentrated eluent to said separation column.

18. The improved process according to claim 17 wherein both the extra-pure water stream and the correspondingly more concentrated eluent stream are each preliminarily conveyed through a purification column upstream.

19. An apparatus for use in combination with a separation column of a chromatograph for the detection of components down to the ppb-range (1 part per $10^9$ parts) in a specimen solution, said apparatus comprising:

a first and second pre-enrichment column disposed upstream of said separation column;

a two-headed feed pump means, operating at a constant flow rate;

valve means disposed between said first and second pre-enrichment columns and said two-headed feed pump means, said valve means altering connection of said pre-enrichment columns into the stream of more concentrated eluent or extra-pure solvent with a change in the direction of flow through said pre-enrichment columns;

first conduit means for the transport of a more concentrated eluent from said two-headed feed pump means to a mixing point;

second conduit means for the transport of extra-pure solvent from said two-headed feed pump means to said mixing point; and specimen feed apparatus means disposed between said two-headed feed pump means and the mixing means, whereby the specimen of interest is introduced into said extra-pure solvent prior to the mixing point, wherein the extra-pure solvent is combined with said more concentrated eluent for introduction into said separation column.

* * * * *